US010881645B2

(12) United States Patent
Spindler, Jr. et al.

(10) Patent No.: US 10,881,645 B2
(45) Date of Patent: Jan. 5, 2021

(54) METHODS FOR CONTROLLING BLOOD PRESSURE AND REDUCING DYSPNEA IN HEART FAILURE

(71) Applicant: Chiesi Farmaceutici S.p.A., Parma (IT)

(72) Inventors: Edward C. Spindler, Jr., Fayetteville, GA (US); Loretta M. Itri, Westfield, NJ (US); Gregory Williams, Bernardsville, NJ (US); Ming-yi Hu, Randolph, NJ (US)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 14/064,137

(22) Filed: Oct. 26, 2013

(65) Prior Publication Data

US 2014/0121247 A1     May 1, 2014

Related U.S. Application Data (60) Provisional application No. 61/719,127, filed on Oct. 26, 2012.

(51) Int. Cl.
*A61K 31/4422* (2006.01)
*A61P 9/08* (2006.01)
*A61K 9/00* (2006.01)

(52) U.S. Cl.
CPC ........ *A61K 31/4422* (2013.01); *A61K 9/0019* (2013.01)

(58) Field of Classification Search
CPC ............ A61K 31/4418; A61K 31/4422; A61K 9/0019
USPC .......................................... 514/356; 546/321
See application file for complete search history.

(56) References Cited

U.S. PATENT DOCUMENTS

| 5,739,152 A | 4/1998 | Andersson et al. |
| 5,856,346 A | 1/1999 | Andersson et al. |
| 6,350,877 B1 | 2/2002 | Mattson et al. |
| 2011/0112030 A1 | 5/2011 | Arculus-Meanwell et al. |
| 2012/0004188 A1 | 1/2012 | Belardinelli |
| 2012/0088804 A1 | 4/2012 | Motheram et al. |
| 2015/0094344 A1 | 4/2015 | Williams |

FOREIGN PATENT DOCUMENTS

| GB | 2459983 | 4/2010 |
| WO | 2010014234 A1 | 2/2010 |
| WO | 2010014727 A1 | 2/2010 |
| WO | 2011159706 | 12/2011 |
| WO | 212135617 | 10/2012 |

OTHER PUBLICATIONS

Clinical Trial NCT00803634, updated Sep. 12, 2011 as per ClinicalTrials.gov archive, http://clinicaltrials.gov/archive/NCT00803634/2011_09_12 accessed from the internet on Oct. 20, 2014.*
Kirk et al. Crit. Pathways in Cardiol. 2008, 7, 103-110.*
Huraux et al. Anesth Analg. 1997, 85 (5), 1000-1004, Abstract.*
Kieler-Jensen et al., Acta Anaesthesiol Scan, 2000, 44: 186-193.
Peacock et al., Congest Heart Fail, 2010, 16: 55-59.
The Medicines Company, US NIH Clinical Trial Proposal, Jun. 2012.
International Search Report, dated Feb. 28, 2014, in the PCT Application No. PCT/US2013/066990.
International Preliminary Report on Patentability, dated Apr. 28, 2015, in the PCT Application No. PCT/US2013/066990.
Erickson et al., Clevidipine: A short-acting intravenous dihydroyridine calcium channel blocker for the management of hypertension, Pharmacotherapy, vol. 30, No. 5, 2010, 515-528.
The Medicines Company, 'Clevidipine in the Treatment of Blood Pressure in Patients With Acute Heart Failure (PRONTO).' U.S. NIH Clinical Trial Proposal, Last Verified on Jun. 2012, pp. 1-8. entire document.
Allen et al., Management of acute decompensated heart failure, Can. Med. Assoc. J., 2007, 176, 797.
Cotter et al., Physician-determined worsening heart failure: a novel definition for early worsening heart failure in patients hospitalized for acute heart failure—association with signs and symptoms, hospitalization duration, and 60-day outcomes, Cardiology 2010, 115, 29.
Cotter et al., The PROTECT pilot study: a randomized, placebo-controlled, dose-finding study of the adenosine A1 receptor antagonist rolofylline in patients with acute heart failure and renal impairment, J. Card. Fail. 2008, 14, 631.
Dickstein et al., ESC guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM), Eur. J. Heart Fail. 2008; 10, 933.
Fonarow et al., Admission B-type natriuretic peptide levels and in-hospital mortality in acute decompensated heart failure, J. Am. Coll. Cardiol. 2007, 49, 1943.
3heorghiade & Pang, Acute heart failure syndromes, J. Am. Coll. Cardiol. 2009, 53, 557.

(Continued)

*Primary Examiner* — Irina Neagu
(74) *Attorney, Agent, or Firm* — Maryellen Feehery Hank; Vorys, Sater, Seymour and Pease LLP (57) ABSTRACT

Methods for controlling, maintaining, or reducing blood pressure, and/or for treating, preventing, or alleviating symptoms such as dyspnea, in a patient suffering from or susceptible to acute heart failure. The methods involve the administration of an effective amount of a pharmaceutical composition comprising a short acting dihydropyridine compound such as clevidipine. The pharmaceutical composition may be administered at an initial dose, and if blood pressure is not controlled or maintained within a target blood pressure range or reduced to within a target blood pressure range, the initial dose may be titrated to achieve a blood pressure within the target blood pressure range. The patient may have a systolic blood pressure of about 120 mmHg or above.

10 Claims, 2 Drawing Sheets

(56) References Cited

OTHER PUBLICATIONS

Gheorghiade et al., Short-term clinical effects of tolvaptan, an oral vasopressin antagonist, in patients hospitalized for heart failure: the EVEREST Clinical Status Trials, JAMA 2007, 297, 1332.

Hogg & McMurray, Evaluating dyspnoea in acute heart failure: progress at last!, Eur. Heart J. 2010, 31, 771.

Hunt et al., Focused update incorporated into the ACC/AHA 2005 Guidelines for the Diagnosis and Management of Heart Failure in Adults a Report of the American College of Cardiology Foundation/ American Heart Association Task Force on Practice Guidelines Developed in Collaboration With the International Society for Heart and Lung Transplantation, J. Am. Coll. Cardiol. 2009, 53, e1.

Kirk et al., Acute heart failure treatment, Crit. Pathways in Cardiol. 2008, 7, 103-110.

Majure et al., Update on the Management of Acute Decompensated Heart Failure; Curr. Treatment Options Cardiovasc. Med. 2011, 13, 570.

McMurray et al., Effects of tezosentan on symptoms and clinical outcomes in patients with acute heart failure: the VERITAS randomized controlled trials, JAMA 2007, 298, 2009-19.

Mebazaa et al., Practical recommendations for prehospital and early in-hospital management of patients presenting with acute heart failure syndromes, Crit. Care Med. 2008, 36, S129.

Mebazaa et al., The impact of early standard therapy on dyspnoea in patients with acute heart failure: the URGENT-dyspnoea study, Eur. Heart J.2010, 31, 832.

Metra et al., Advanced chronic heart failure: A position statement from the Study Group on Advanced Heart Failure of the Heart Failure Association of the European Society of Cardiology, Eur. J. Heart Fail. 2007, 9, 684.

Metra et al., Dyspnoea and worsening heart failure in patients with acute heart failure: results from the PRE-RELAX-AHF study, Eur. J. Heart Fail. 2010, 12, 1130.

O'Connor et al., Demographics, clinical characteristics, and outcomes of patients hospitalized for decompensated heart failure: observations from the IMPACT-HF registry, J. Card. Fail. 2005; 11, 200-5.

Peacock et al., Clevidipine for severe hypertension in acute heart failure: a VELOCITY trial analysis, Congest. Heart Fail. 2010, 16, 55-9.

Publication Committee for the VMAC Investigators, Intravenous nesiritide vs nitroglycerin for treatment of decompensated congestive heart failure: a randomized controlled trial, JAMA 2002, 287, 1531.

Torre-Amione et al., Early worsening heart failure in patients admitted for acute heart failure: time course, hemodynamic predictors, and outcome, J. Card. Fail. 2009, 15, 639.

Weatherley et al., Early worsening heart failure in patients admitted with acute heart failure—a new outcome measure associated with long-term prognosis?, Fundam. Clin. Pharmacol. 2009, 23, 633.

Yancy et al., Clinical presentation, management, and in-hospital outcomes of patients admitted with acute decompensated heart failure with preserved systolic function: a report from the Acute Decompensated Heart Failure National Registry (ADHERE) Database, J. Am. Coll. Cardiol. 2006; 47, 76.

Peacock IV, MD, et al., "Clevidipine for Severe Hypertension in Acute Heart Failure: A VELOCITY Trial Analysis"; Wiley Periodicals, Inc.; 16:55-59; Mar./Apr. 2010.

Deeks, et al., "Clevidipine—A Review of its Use in the Management of Acute Hypertension"; American Journal Cardiovasc Drugs 2009; 9 (2); 117-134.

\* cited by examiner

METHODS FOR CONTROLLING BLOOD PRESSURE AND REDUCING DYSPNEA IN HEART FAILURE

CROSS-REFERENCE TO RELATED APPLICATIONS

This application claims the benefit of U.S. Provisional Application No. 61/719,127, filed on Oct. 26, 2012, the contents of which are incorporated by reference herein, in their entireties and for all purposes.

FIELD OF INVENTION

The present invention is directed to therapies for patients who are suffering from or are susceptible to acute heart failure. In particular, the present invention relates to methods of controlling, maintaining, or reducing blood pressure, and to methods of treating, preventing, or alleviating symptoms, in patients suffering from or susceptible to acute heart failure. The present invention also relates to pharmaceutical compositions for use in such methods.

BACKGROUND OF THE INVENTION

Acute heart failure (AHF) or acute decompensated heart failure (ADHF) represents a heterogeneous group of disorders that are defined by a gradual or rapid change in signs and symptoms typically including dyspnea (shortness of breath), edema (fluid retention), and fatigue, and which require rapid intervention (Gheorghiade et al., *Circulation* 2005, 112, 3958). These symptoms are primarily the result of severe pulmonary congestion due to elevated left ventricular (LV) filling pressures, which may or may not be the result of low cardiac output, and as such the diagnosis of AHF is not clear cut. While AHF is generally used to qualify heart failure in patients with no history of heart failure, frequently, AHF occurs in patients with previously established myocardial dysfunction (systolic or diastolic) such as in congestive heart failure and who suddenly present an exacerbation of symptoms or signs after a period of relative stability (Allen et al., *Can. Med. Assoc. J.* 2007, 176, 797). Nevertheless, the high prevalence of this condition and the high rates of morbidity and mortality associated with it drive the development of new treatment options. The difficulties surrounding treatment begin with the lack of a clear definition and insufficient understanding of the underlying pathophysiology of the disease. Very few effective treatments are available for AHF that improve clinical outcomes (Mebazaa et al. *Crit. Care Med.* 2008, 36, S129). Diuretics and vasodilators have been used for a long time to successfully stabilize patients with AHF. However, the current therapies lack the evidence of long-term benefits, especially in reducing mortality in AHF patients. Moreover, the current therapies are associated with serious adverse effects, such as arrhythmias, renal impairment, and hypotension due to their vasodilatory effects.

Dyspnea and other symptoms and signs of cardiopulmonary congestion are the primary AHF manifestations (Kirk et al., *Clin. Courier* 2006, 23, No 56) and require immediate attention from the attending physician. As such, beyond end organ perfusion and function, the use of therapeutics predominantly targets the relief of dyspnea (Majure et al. *Curr. Treatment Options Cardiovasc. Med.* 2011, 13, 570). Currently, dyspnea relief is an acceptable primary efficacy end point in phase III AHF studies for regulatory approval by governmental agencies. Besides being the primary symptom of AHF, dyspnea is also the primary cause of patient hospitalization. Dyspnea is often associated with signs of fluid overload, including pulmonary and/or peripheral congestion (Gheorghiade & Pang, *J. Am. Coll. Cardiol.* 2009, 53, 557; Publication Committee for the VMAC Investigators, *JAMA* 2002, 287, 1531; McMurray et al., *JAMA* 2007, 298, 2009; Gheorghiade et al., *JAMA* 2007, 297, 1332). Reduction of dyspnea and stabilization of the patient are the main goals of AHF therapy during the first few hours of admission to a health care facility. It is believed that achievement of this goal has a direct impact on the patient's quality of life.

AHF may present with varying degrees of systolic blood pressure (SBP), from low to severe, each with unique therapeutic recommendations (Kirk et al., *Crit. Pathways in Cardiol.* 2008, 7, 103). Hypertension (defined as SBP of at least 140 mmHg) in the setting of AHF is found in more than 50% of AHF patients presenting to hospitals for treatment. The chief symptom is severe respiratory distress manifested by often severe dyspnea. A second group of patients with AHF may also present to hospitals with moderate to severe dyspnea, but have SBP in the range of 110 mmHg to 140 mmHg. Despite the apparent normality of their SBP, these patients are profoundly ill and require urgent treatment of their pulmonary congestion to alleviate their dyspnea and to restore their normal arterial blood oxygen levels.

Despite the fact that AHF is the most prevalent cause of hospitalization in the population older than 65 years, no new therapies have been approved and accepted globally for more than the past 25 years (Metra et al., *Eur. J. Heart Fail.* 2010, 12, 1130; Dickstein et al., *Eur. J. Heart Fail.* 2008; 10, 933; Gheorghiade & Pang, *J. Am. Coll. Cardiol.* 2009, 53, 557; Hunt et al., *J. Am. Coll. Cardiol.* 2009, 53, e1; Metra et al., *Eur. J. Heart Fail.* 2007, 9, 684). As shown in recent AHF clinical studies, moderate to marked relief of dyspnea occurs in only 40-60% of patients during the first days after admission (O'Connor et al., *J. Card. Fail.* 2005; 11, 200; Yancy et al., *J. Am. Coll. Cardiol.* 2006; 47, 76; Fonarow et al., *J. Am. Coll. Cardiol.* 2007, 49, 1943; Cotter et al., *J. Card. Fail.* 2008, 14, 631; Mebazaa et al., *Eur. Heart J.* 2010, 31, 832; Hogg & McMurray, *Eur. Heart J.* 2010, 31, 771). Moreover, 10-20% of AHF patients develop recurrent symptoms and worsening heart failure or die during the first few days after admission (Weatherley et al., *Fundam. Clin. Pharmacol.* 2009, 23, 633; Cotter et al., *Cardiology* 2009, 115, 29; Torre-Amione et al., *J. Card. Fail.* 2009, 15, 639). The hospitalization for AHF patients, comprising the time spent in the intensive care unit (ICU), represents an increasing overall burden for health care costs.

Therefore, there remains a need for novel therapies for hypertensive AHF with respect to an antihypertensive drug that provides an optimal balance of efficacy, precision (titratability), and safety in patients. A post-hoc subgroup analysis reports that clevidipine, a calcium channel blocker from the dihydropyridine family of molecules, may be useful in a certain patient population group for treatment of patients with severe hypertension (>180 mmHg) with AHF. Peacock et al., *Congest. Heart Fail.* 2010, 16, 55-9. The relatively small number of patients observed in this subgroup analysis, however, prevents broad-based conclusions from being drawn. Id. at 55. For example, the analysis does not address the use of clevidipine for treating dyspnea in patients outside of the patient population group. Moreover, dihydropyridine calcium channel blockers can produce negative inotropic effects and exacerbate heart failure, indicating that heart failure patients be monitored carefully when treated with such agents (see Cleviprex® Labeling (8 Dec. 2011) at p. 5).

As such, there remains a need for further investigation and development of novel approaches to alleviate dyspnea in moderately hypertensive or normotensive AHF patients without creating a hypotensive condition.

SUMMARY OF THE INVENTION

The present invention provides therapies for patients who are suffering from or are susceptible to AHF. In particular, the present invention relates to the use of a short acting dihydropyridine compound such as clevidipine for controlling, maintaining, or reducing blood pressure, and for treating, preventing, or alleviating symptoms such as dyspnea, in a patient suffering from or susceptible to AHF. The patient may have an SBP of about 160 mmHg or above (e.g., severe hypertension), between about 140 mmHg and about 160 mmHg (e.g., moderate hypertension), or about 120 mmHg to about 140 mmHg (e.g., normotension). The present invention also relates to pharmaceutical compositions comprising a short acting dihydropyridine compound such as clevidipine and methods of preparing the pharmaceutical compositions.

Therefore, in one aspect, the present invention provides a method for controlling, maintaining, or reducing blood pressure in a patient suffering from or susceptible to AHF. This method comprises administering to the patient an effective amount of a pharmaceutical composition comprising a short acting dihydropyridine compound such as clevidipine so as to control or maintain the patient's blood pressure within a target blood pressure range, and/or to reduce the patient's blood pressure to within a target blood pressure range.

In another aspect, the present invention relates to a method of treating, preventing, or alleviating symptoms in a patient suffering from or susceptible to AHF. This method comprises administering to the patient an effective amount of a pharmaceutical composition comprising a short acting dihydropyridine compound such as clevidipine. The symptoms in the patient suffering from or susceptible to AHF may include dyspnea, edema, and fatigue.

Each of the methods described herein may further comprise administering the pharmaceutical composition at an initial dose, and if blood pressure is not controlled or maintained within a target blood pressure range or reduced to within a target blood pressure range, titrating the dose to achieve a blood pressure within the target blood pressure range. Titration may require multiple dosage adjustments, and the time interval between each dose adjustment may be about 1 to about 10 minutes. Each dose adjustment may double, or less than double, the previous dose. In some instances, the dose may be adjusted downward in order to control or maintain the patient's blood pressure within the target blood pressure range.

In certain embodiments, the pharmaceutical composition may be administered intravenously. For example, the pharmaceutical composition may be administered as a bolus, as a continuous infusion, or as a combination of a bolus and a continuous infusion.

In particular embodiments, the present invention relates to a method of reducing dyspnea in a patient in need thereof who has AHF and either has a baseline (prior to administration of the pharmaceutical composition) SBP between about 120 mmHg and less than 160 mmHg, or is normotensive as determined by the patient's baseline SBP. The method may comprise administering a pharmaceutical composition comprising clevidipine to the patient. The patient may have a baseline dyspnea score of at least about 50 mm using a 100 mm visual analog scale (VAS), and the reduction in dyspnea may be determined by a decrease in a dyspnea score using VAS. The pharmaceutical composition may be administered as an intravenous infusion at a rate between about 1 mg/h and about 32 mg/h of clevidipine, and for duration of about 30 minutes to about 72 hours. In some embodiments, the intravenous infusion may be administered at an initial rate of about 2 mg/h of clevidipine, and this initial rate may be maintained for at least about 90 seconds. The method may further comprise titrating the intravenous infusion to a rate that maintains the patient's SBP at no less than about 110 mmHg. The method may additionally control, maintain, or reduce the patient's SBP. In the case where the patient is normotensive, the patient's baseline SBP may be between about 120 mmHg and about 140 mmHg.

An additional aspect of the present invention relates to a pharmaceutical composition comprising an effective amount of a short acting dihydropyridine compound for use in the methods of the present invention, including for controlling, maintaining, or reducing blood pressure and for treating, preventing, or alleviating symptoms such as dyspnea in a patient suffering from or susceptible to AHF. The pharmaceutical composition may be an emulsion and, in some embodiments, may comprise a lipid at about 2% to about 30% (w/v) and an emulsifier at about 0.2 mg/ml to about 20 mg/ml. The pharmaceutical composition may further comprise one or more agents selected from the group consisting of an antimicrobial agent, a tonicity modifier, an antioxidant, and a co-emulsifier. In embodiments in which the short acting dihydropyridine is clevidipine, the quantity of clevidipine in the pharmaceutical composition may be about 0.001 mg/ml to about 20 mg/ml.

A further aspect of the present invention relates to a method of preparing a pharmaceutical composition of the invention. The method may comprise admixing a short acting dihydropyridine compound such as clevidipine with a pharmaceutically acceptable carrier or diluent. The method may also comprise admixing the short acting dihydropyridine compound with a lipid, an emulsifier, and water, and may further comprise adding an antimicrobial agent, a tonicity modifier, an antioxidant, and/or a co-emulsifier. The method may additionally comprise adjusting the pH of the admixture to between about 6.0 and about 8.8, and/or placing the pharmaceutical composition in a sterile pre-filled syringe.

BRIEF DESCRIPTION OF THE FIGURES

The following Detailed Description, given by way of example, but not intended to limit the invention solely to the specific embodiments described, may best be understood in conjunction with the accompanying drawings, in which:

FIG. 2 shows the mean change in SBP and the mean VAS scores over time in patients who were administered clevidipine and in patients who were administered SOC therapy.

DETAILED DESCRIPTION OF THE INVENTION

The present invention is based on the discovery that clevidipine, a short acting dihydropyridine compound, is effective in controlling, maintaining, and reducing blood pressure in a patient suffering from or susceptible to AHF. The present invention is also based on the discovery that clevidipine is effective in treating, preventing, and alleviating symptoms associated with AHF, such as dyspnea, in a patient suffering from or susceptible to AHF. Thus, the present invention relates to the use of a short acting dihydropyridine compound such as clevidipine for controlling, maintaining, or reducing blood pressure, and for treating, preventing, or alleviating symptoms such as dyspnea, in a patient suffering from or susceptible to AHF. The present invention also relates to pharmaceutical compositions comprising a short acting dihydropyridine compound such as clevidipine and methods of preparing the pharmaceutical compositions.

Short Acting Dihydropyridine Compounds

The short acting dihydropyridine compound of the invention may have a half-life in plasma of less than about 30 minutes, preferably less than about 10 minutes, more preferably less than about 5 minutes, most preferably less than about 2 minutes. The short acting dihydropyridine compound may have a rapid onset of activity as well as a rapid offset of activity. A short acting compound reaches steady plasma drug concentration quickly (e.g., within less than about one hour after starting drug administration), and gets cleared quickly (e.g., within about five hours after ending drug administration). The full offset of activity may be achieved within about one hour, preferably within about 5 to about 15 minutes. The short acting dihydropyridine compound is preferably clevidipine.

Clevidipine

Clevidipine is a dihydropyridine L-type calcium channel blocker. Having a very short half-life (about 1 minute), clevidipine exhibits rapid onset of activity (2 to 4 minutes) and rapid offset of activity (full offset of activity in 5 to 15 minutes). The chemical structure of clevidipine is shown in Formula I.

Formula I

The term "clevidipine" as used herein encompasses the compound of Formula I, as well as tautomeric, enantiomeric and diastereomeric forms thereof, and racemic mixtures thereof, and pharmaceutically acceptable salts, isomers, stereo isomers, crystalline and amorphous forms of these compounds. These alternative forms and salts, processes for their production, and pharmaceutical compositions comprising them, are well known in the art and set forth in U.S. Pat. Nos. 5,856,346, 5,739,152, and 6,350,877, as well as International Patent Application Nos. PCT/US09/004399 and PCT/US09/52127, which are all incorporated herein by reference.

Clevidipine is an ideal parenteral antihypertensive medication as it provides an optimal balance of efficacy (the ability to rapidly reduce blood pressure to target levels), safety (the ability to avoid overshoot hypotension, and absence of toxicity and side-effects), and precision (the ability to hit and maintain blood pressure target levels while avoiding overshoot, and the speed with which titration can be accomplished). Additionally, in patients with pre-existing or inter-current hepatic or renal dysfunction, agents that are metabolized renally or hepatically are unsuitable.

Because of its rapid onset and offset, clevidipine can be titrated in a manner allowing rapid upward and downward adjustments in dose as clinical circumstances dictate, and substantially reducing the risk of overshoot hypotension, which is especially important in hemodynamically unstable patients. Clevidipine is rapidly metabolized via blood and tissue esterases, and does not accumulate in tissues. It can therefore be safely administered to hepatically and renally compromised patients.

Other Short Acting Dihydropyridine Compounds

Other short acting dihydropyridine compounds may include compounds corresponding to formula I as set forth in U.S. Pat. No. 5,739,152, and formula I as set forth in U.S. Pat. No. 5,856,346, as well as tautomeric, enantiomeric and diastereomeric forms thereof, racemic mixtures thereof, and pharmaceutical acceptable salts, esters, isomers, stereo isomers, crystalline and amorphous forms thereof.

Patients

As used herein, a "patient" upon which the methods of the present invention may be practiced refers to a mammal, preferably a human. Such patients suffer from or are susceptible to AHF.

The patient's baseline blood pressure may be about 160 mmHg or above, or about 140 mmHg or above, or between about 140 mmHg and less than 160 mmHg, or about 120 mmHg or above, or between about 120 mmHg and less than 160 mmHg, or between about 120 mmHg and about 140 mmHg.

Acute Heart Failure (AHF)

AHF may be due to gradual or rapidly worsening heart failure requiring urgent therapy. AHF may also be due to a new onset of heart failure from an acute coronary event, such as a myocardial infarction (MI). Alternatively, AHF may be due to cardiac decompensation resulting from any one or more causes, including but not limited to, neurohormonal imbalance, fluid overload, cardiac arrhythmia, and cardiac ischemia. AHF includes, but is not limited to, ADHF, high output failure, hypertensive heart failure, vascular heart failure, de novo heart failure, pulmonary edema, cardiogenic shock, cardiac failure, acutely decompensated chronic heart failure, acute coronary syndrome with heart failure, and right heart failure. Associated co-morbidities may include history of coronary artery disease (CAD), hypertension, atrial fibrillation (AF) or history of AF, diabetes, arteriosclerotic heart disease, renal dysfunction or insufficiency, chronic obstructive pulmonary disease, infections, or anemia.

Symptoms of Acute Heart Failure

Symptoms accompanying AHF may primarily result from severe pulmonary congestion due to elevated LV filling pressures with or without limitations in cardiac output. Such symptoms may include, but are not limited to, dyspnea (shortness of breath), fatigue and weakness, swelling of the extremities (edema) or of the abdomen (ascites), rapid or irregular heartbeat (palpitations), fluid retention, and chest pain.

Dyspnea is a primary symptom of AHF and the main cause of patient hospitalization. It is often associated with signs of fluid overload, including pulmonary and/or peripheral congestion. Dyspnea may be evaluated using a 100 mm VAS. Patients upon which the methods of the present invention may be practiced may be experiencing dyspnea with a baseline score of ≥50 mm.

Medical History of the Patient

In the past, the patient may have suffered from hypertensive encepthalopathy, aortic dissection, acute renal failure, acute pulmonary edema, or acute MI. The patient may also have previously suffered from or may have been susceptible to heart failure and/or dyspnea. Further, the patient may have suffered from a heart disease, an acute coronary event such as an MI, arteriosclerotic heart disease, atrial fibrillation, diabetes, renal dysfunction or insufficiency, a family history of stroke, a previous stroke, a previous transient ischemic attack, chronic obstructive pulmonary disease, infections, anemia, high cholesterol, or sickle cell anemia. In addition, the patient may have suffered from thrombosis. The thrombosis may be a large vessel disease or a small vessel disease. The large vessel disease may be atherosclerosis, vasoconstriction, aortic, carotid or vertebral artery dissection, an inflammatory disease of a blood vessel wall, noninflammatory vasculopathy, moyamoya disease, or fibromuscular dysplasia. The inflammatory disease of a blood vessel wall may be selected from the group consisting of Takayasu arteritis, giant cell arteritis, and vasculitis. The small vessel disease may be lipohyalinosis, fibrinoid degeneration, or microatheroma.

The patient may have previously received additional treatments including but not limited to diuretics, vasodilators, inotropes/inodilators, vasopressin receptor antagonists, opiates, relaxin, istaroxime, cenderitide, nitroxyl donors, antihypertensives, or anticoagulants. The diuretics may be nonpotassium sparing diuretics (loop diuretics), thiazide diuretics, or potassium sparing diuretics. Examples of diuretics include, but are not limited to, furosemide, bumetanide, bendroflumethiazide, amiloride, and spironolactone. Vasodilators may include nitrates such as nitroglycerin and isosorbide dinitrate, nesiritide, nitroprusside, or cinaciguat. Inotropes may include dopamine, dobutamine, milrinone, and levosimendan. The antihypertensive drug may be, for example, thiazide diuretics, angiotensin-converting enzyme (ACE) inhibitors, calcium channel blockers, beta blockers, or angiotensin II receptor antagonists. The anticoagulation drug may be warfarin, aspirin, or antiplatelet drugs.

Methods of Treating Patients with Acute Heart Failure

The present invention provides a method for controlling, maintaining, or reducing blood pressure in a patient suffering from or susceptible to AHF. This method comprises administering to the patient an effective amount of a pharmaceutical composition comprising a short acting dihydropyridine compound such as clevidipine so as to control or maintain the patient's blood pressure within a target blood pressure range, and/or to reduce the patient's blood pressure to within a target blood pressure range. The effective amount of the pharmaceutical composition may be an amount that controls or maintains the patient's blood pressure within a target blood pressure range and/or reduces the patient's blood pressure to within a target blood pressure range. For example, the effective amount of the pharmaceutical composition may be an amount that controls or maintains the patient's blood pressure at or near the lower limit of the target blood pressure range, and/or reduces the patient's blood pressure to or near the lower limit of the target blood pressure range.

The present invention also relates to a method of treating, preventing, or alleviating symptoms in a patient suffering from or susceptible to AHF. This method comprises administering to the patient an effective amount of a pharmaceutical composition comprising a short acting dihydropyridine compound such as clevidipine. The symptoms may include dyspnea, edema, and fatigue. In some embodiments, the effective amount of the pharmaceutical composition may be an amount that controls or maintains the patient's blood pressure within a target blood pressure range and/or reduces the patient's blood pressure to within a target blood pressure range. In some instances, the effective amount of the pharmaceutical composition may be an amount that controls or maintains the patient's blood pressure at or near the lower limit of the target blood pressure range, and/or reduces the patient's blood pressure to or near the lower limit of the target blood pressure range. In certain embodiments, the effective amount of the pharmaceutical composition may be an amount that is subtherapeutic for the treatment of hypertension. In particular embodiments, if the patient is normotensive and experiencing dyspnea as a symptom of AHF, the effective amount of the pharmaceutical composition may be a lower dose than what would be typically administered to a patient to treat hypertension.

In certain embodiments, the patient may experience an alleviation of the symptoms within about 5 hours or less once the administration of the pharmaceutical composition comprising the short acting dihydropyridine compound is initiated. In some instances, symptoms such as dyspnea may be reduced (e.g., improvement in VAS score) within about 5 hours, or within about 3 hours, of initiating the administration of the pharmaceutical composition comprising the short acting dihydropyridine compound.

In general, the effective amount of the pharmaceutical composition comprising a short acting dihydropyridine compound (e.g., clevidipine) may vary depending upon the stated goals, the physical characteristics of the patient, the nature and severity of the AHF and/or its signs and symptoms, existence of related or unrelated medical conditions, the nature of the short acting dihydropyridine compound, the composition comprising the short acting dihydropyridine compound (e.g., clevidipine), the means of administering the drug to the subject, and the administration route.

A physician may determine a target blood pressure range of SBP for the patient. The difference between the upper and lower limits of the target blood pressure range may not be less than about 20 mmHg and may not be more than about 40 mmHg. In certain embodiments, the lower limit of the target blood pressure range may not be below about 110 mmHg. The patient's baseline blood pressure may be about 160 mmHg or above, or about 140 mmHg or above, or between about 140 mmHg and less than 160 mmHg, or about 120 mmHg or above, or between about 120 mmHg and less than 160 mmHg, or between about 120 mmHg and about 140 mmHg. In some embodiments, if the patient's baseline blood pressure is about 140 mmHg or above, the target blood pressure range may be at least 15% less than the patient's baseline blood pressure.

Each of the methods described herein may further comprise administering the pharmaceutical composition at an initial dose, and if blood pressure is not controlled or maintained within the target blood pressure range or reduced to the target blood pressure range, titrating the dose to achieve a blood pressure within the target blood pressure range. Titration may require multiple dosage adjustments, and the time interval between each dose adjustment may be about 1 to about 10 minutes. Each dose adjustment may double, or less than double, the previous dose. In some instances, the dose may be adjusted downward in order to control or maintain the patient's blood pressure within a target blood pressure range.

According to the present invention, the pharmaceutical compositions are preferably administered to the subject in a parenteral dosage form, more preferably in an intravenous dosage form. For example, the pharmaceutical composition may be administered as a bolus, as a continuous infusion, or as a combination of a bolus and a continuous infusion. In certain embodiments, the pharmaceutical composition may be administered continuously for a period of at least about 30 minutes to 96 hours.

In embodiments in which the short acting dihydropyridine compound is clevidipine, the pharmaceutical composition may be administered as a continuous intravenous infusion. In some embodiments, the intravenous infusion is administered at a rate of about 1 to about 32 mg/h of clevidipine. In certain embodiments, the initial dose may be about 0.1 to about 20 mg/h of clevidipine, preferably about 1 to about 2 mg/h of clevidipine. The titrating dose may be about 0.1 to about 50 mg/h, or about 1 to about 32 mg/h, or about 1 to about 16 mg/h, or about 4 to about 6 mg/h of clevidipine. The time interval between dosage adjustments is about 1 to about 30 minutes, or about 2 to about 20 minutes, or about 5 to about 10 minutes. In particular embodiments, the dose may be doubled at short (e.g., 60 seconds) intervals initially, and as the SBP of the patient approaches the target blood pressure range, the increase in doses should be less than doubling and the time between dose adjustments may be lengthened to about every 5 to about every 10 minutes.

The target blood pressure range may be achieved within about 30 minutes of initiating the administration of the pharmaceutical composition comprising the short acting dihydropyridine compound. During this initial 30 minute period, the pharmaceutical composition comprising the short acting dihydropyridine compound may be administered as a monotherapy with the exception of diuretics and morphine. In some embodiments, if the target blood pressure range is not achieved within about 30 minutes or is not maintained thereafter, an alternative antihypertensive agent may be used, with or without stopping the administration of the pharmaceutical composition comprising the short acting dihydropyridine compound.

In particular embodiments, the present invention relates to a method of reducing dyspnea in a patient in need thereof who has AHF and either has a baseline SBP between about 120 mmHg and less than 160 mmHg, or is normotensive as determined by the patient's baseline SBP. The method may comprise administering a pharmaceutical composition comprising clevidipine to the patient. The patient may have a baseline dyspnea score of at least about 50 mm using a 100 mm VAS, and the reduction in dyspnea may be determined by a decrease in a dyspnea score using VAS. The pharmaceutical composition may be administered as an intravenous infusion at a rate between about 1 mg/h and about 32 mg/h of clevidipine, and for a duration of about 30 minutes to about 72 hours. In some embodiments, the intravenous infusion may be administered at an initial rate of about 2 mg/h of clevidipine, and this initial rate may be maintained for at least about 90 seconds. The method may further comprise titrating the intravenous infusion to a rate that maintains the patient's SBP at no less than about 110 mmHg. The method may additionally, control, maintain, or reduce the patient's SBP. In the case where the patient is normotensive, the patient's baseline SBP may be between about 120 mmHg and about 140 mmHg.

Discontinuation of administering the short acting dihydropyridine compound may allow return of the blood pressure to a pre-treatment level in the patient, for example, within about 30 minutes or less. The short half-life of clevidipine results in a rapid offset of action with the return of blood pressure to pre-treatment levels within about 5 to about 15 minutes of the discontinuation of clevidipine.

Administration of clevidipine may also achieve an amelioration in acute cardiac decompensation events including, but not limited to, treating pulmonary and systemic congestion with or without low cardiac output resulting from LV diastolic pressure, controlling/reducing blood pressure, preventing myocardial injury, improving renal impairment, and treating arrhythmia. A reversal of acute cardial decompensation may lead to a decrease in circulating levels of brain natriuretic peptide (BNP) and reduce the length of hospital stay of AHF patients.

Pharmaceutical Compositions Useful for Treating Patients with Acute Heart Failure Pharmaceutical Compositions The pharmaceutical composition of the present invention may be for controlling, maintaining, or reducing blood pressure in a patient suffering from or susceptible to AHF, or may be for treating, preventing or alleviating symptoms in a patient suffering from or susceptible to AHF, in accordance to the methods of the present invention.

The pharmaceutical composition may comprise short acting dihydropyridine such as clevidipine in an amount of about 0.001 to about 20 mg/ml, or about 0.005 to about 1 mg/ml, or about 0.01 to about 1 mg/ml, or about 0.05 to about 0.5 mg/ml. In particular embodiments in which the short acting dihydropyridine is clevidipine, the amount may be about 0.5 mg/ml.

The pharmaceutical composition may further comprise a pharmaceutically acceptable carrier or diluent. Carriers, diluents, and excipients suitable in the pharmaceutical composition are well known in the art. Suitable pharmaceutical compositions include formulations (e.g., solutions and emulsions) described in U.S. Pat. Nos. 5,856,346, 5,739,152, and 6,350,877, as well as International Patent Application Nos. PCT/US09/004399 and PCT/US09/52127, which are all incorporated herein by reference.

The pharmaceutical composition may have a pH of about 5.6 to about 10.0, or about 6.0 to about 8.8, or about 6.0 to about 8.0. For example, the pH may be about 6.2, 6.5, 6.75, 7.0, or 7.5.

The pharmaceutical composition may be an emulsion, freeze dried material from the emulsion, or a concentrate for reconstitution (self-emulsifying system). In certain embodiments, the pharmaceutical composition is an emulsion. The emulsion may comprise a short acting dihydropyridine compound, a lipid, an emulsifier, and/or water or a buffer. The lipid may be present in amount of about 2% to about 30% (w/v), and may be selected from the group consisting of soybean oil, safflower seed oil, olive oil, cottonseed oil, sunflower oil, sesame oil, peanut oil, corn oil, medium chain triglycerides, triacetin, propylene glycol diesters, monoglycerides, and a mixture of two or more thereof. The emulsifier may be present at about 0.2 to about 20 mg/ml, and be selected from the group consisting of egg yolk phospholipids, soybean phospholipids, synthetic phosphatidyl cholines, purified phosphatidyl cholines and hydrogenated phosphatidyl choline, and mixtures of two or more thereof.

The pharmaceutical composition may also comprise an antimicrobial agent, a tonicity modifier, an antioxidant, and/or a co-emulsifier. The antimicrobial agent may be present in an amount of about 0.01 to about 1 mg/ml, and may be selected from the group consisting of benzyl alcohol, ethylenediaminetetraacetic acid (EDTA), sodium ascorbate, citric acid, and mixtures, derivatives, and salts thereof. The tonicity modifier may be present in an amount of about 2 to about 30 mg/ml. The antioxidant may be present in an amount of about 0.01 to about 1 mg/ml, and may be selected from the group consisting of sodium ascorbate, sodium citrate, cysteine hydrochloride, sodium bisulfate, sodium metabisulfite, sodium sulfite ascorbyl palmitate, butylated hydroxyanisole (BHA), butylated hydroxytoluene (BHT), propyl gallate, tocopherol, and a pharmaceutically acceptable salt thereof. The co-emulsifier may be present in an amount of about 0.01 to about 2 mg/ml, and may be selected from the group consisting of glycerol (or glycerin), poloxamers, Kolliphor EL® (formerly known as Cremophor®, which is polyethoxylated castor oil), poloxamines, polyoxyethylene stearates, polyoxyethylene sorbitan fatty acid esters, sorbitan fatty acid esters, polysorbates, tocopherol polyethylene glycol succinate, cholic acid, deoxycholic acid, oleic acid, and pharmaceutically acceptable salts thereof.

The pharmaceutical compositions of the present invention may be formulated, for example, for oral, sublingual, intranasal, intraocular, rectal, transdermal, mucosal, topical or parenteral administration. Parenteral administration may include intradermal, subcutaneous (s.c., s.q., sub-Q, Hypo), intramuscular (i.m.), intravenous (i.v. or IV), intraperitoneal (i.p.), intra-arterial, intramedulary, intracardiac, intra-articular (joint), intrasynovial (joint fluid area), intracranial, intraspinal, and intrathecal (spinal fluids). Any device suitable for parenteral injection or infusion of drug formulations may be used for such administration. For example, the pharmaceutical composition may be contained in a sterile pre-filled syringe.

In particular embodiments, the pharmaceutical composition comprising clevidipine is Cleviprex®, which is an oil-in-water emulsion containing soybean oil (200 mg/ml), glycerin (22.5 mg/ml), purified egg yolk phospholipids (12 mg/ml), oleic acid (0.3 mg/ml), disodium edetate (0.05 mg/ml), and sodium hydroxide to adjust pH. Cleviprex® has a pH of 6.0 to 8.0 and is a ready-to-use emulsion.

Preparing Pharmaceutical Compositions

The present invention also relates to methods for preparing the pharmaceutical compositions. The preparation methods may comprise admixing a short acting dihydropyridine compound such as clevidipine with a pharmaceutically acceptable carrier or diluent. The methods may also comprise combining a short acting dihydropyridine compound with a lipid, an emulsifier, and/or water. The methods may further comprise adding one or more agents selected from the group consisting of an antimicrobial agent, a tonicity modifier, an antioxidant, and a co-emulsifier; adjusting the pH of the admixture to about 6.0 to about 8.8, or about 6.0 to about 8.0; and/or placing the medicament in a sterile pre-filled syringe.

The invention will now be further described by way of the following non-limiting examples, which further illustrate the invention, and are not intended, nor should they be interpreted to, limit the scope of the invention.

EXAMPLES

Example 1

Clevidipine Improves the Management of Blood Pressure Associated with Acute Heart Failure A randomized open label 13-center trial enrolled AHF patients with SBP of ≥160 mmHg, sitting dyspnea score ≥50 on a 100 mm VAS, and a physician's clinical diagnosis of AHF with pulmonary congestion by chest auscultation. Patients were excluded if they required endotracheal intubation, had contraindication to clevidipine (i.e., Cleviprex®), received any antihypertensive agent within the previous 2 hours (except short acting non-IV nitrates), had chest pain or electrocardiogram (ECG) changes, suspected aortic dissection, myocardial infarction within 14 days, pregnancy, known liver failure or renal failure, or pancreatitis. Eligible patients were randomized 1:1 to receive either clevidipine or SOC within one hour of emergency department presentation.

At randomization, the treating physician recorded a 30-minute target blood pressure range to reach a minimum of about 15% blood pressure reduction from baseline, in which the difference between the upper and lower limits of the target blood pressure range was about 20 mmHg to about 40 mmHg.

Clevidipine was initiated at 2.0 mg/h for 3 minutes, and then doubled every 3 minutes to a maximum of 32.0 mg/h, until the target blood pressure range was reached. SOC therapy was per institutional standard. During the initial 30 minutes of treatment, the clevidipine or SOC (collectively "study drug") was administered as a monotherapy except in cases of medical necessity or patient safety. If the target blood pressure range was not reached within 30 minutes, or not maintained thereafter, alternative antihypertensive agents were allowed per physician discretion, with or without continuation of the study drug. If a patient on clevidipine failed to achieve the target blood pressure range, additional non-calcium channel blocker antihypertension medication was allowed.

Two populations were analyzed. The "safety" population included all patients receiving any study drug, and was used for all safety analyses. The "confirmed AHF" population or "AHF" population, used for all efficacy analyses, consisted of all safety patients with either (a) a creatine clearance >30 ml/h (estimated by the Cockcroft-Gault formula) and a BNP ≥400 (or N-terminal pro-hormone of brain natriuretic peptide (NTpro-BNP) >900 pg/ml) corrected for obesity by doubling the BNP if the body mass index (BMI) exceeded 35 kg/m$^2$; or (b) chest X-ray evidence of pulmonary congestion.

A total of 104 patients (51 patients receiving clevidipine and 53 patients receiving SOC) were enrolled and treated, and constituted the safety cohort. Of this safety cohort, 19 patients (7 receiving clevidipine, 12 receiving SOC) did not meet the predefined criteria to confirm AHF, 15 patients (7 receiving clevidipine, 8 receiving SOC) lacked evidence of pulmonary congestion, and 4 patients (0 receiving clevidipine, 4 receiving SOC) had protocol deviations such as prior use of antihypersensitive agents or insufficient symptoms. This resulted in an AHF population of 85 patients (44 receiving clevidipine, 41 receiving SOC). Table 1 describes the study population, which shows that demographics, medical histories and baseline characteristics were similar for the safety and AHF cohorts, and that there were no differences between groups based on treatment allocation (Table 1). Overall, the mean baseline VAS score was 65 mm.

TABLE 1

Patient population characteristics and systolic blood pressure targets.

| Characteristics | AHF Population (n = 85) | | Safety Population (n = 104) | |
|---|---|---|---|---|
| | Clevidipine (n = 44) | SOC (n = 41) | Clevidipine (n = 51) | SOC (n = 53) |
| *Demographics* | | | | |
| Age (years)[a] | 62 [15.3] | 60 [13.9] | 62 [14.9] | 60 [14.9] |
| Female | n = 21 (47.7%) | n = 22 (53.7%) | n = 25 (49.0%) | n = 29 (54.7%) |
| African American | n = 32 (72.7%) | n = 34 (82.9%) | n = 39 (76.5%) | n = 44 (83.0%) |
| BMI[a] | 34.6 [9.6] | 34.8 [12.0] | 34.5 [9.2] | 33.5 [11.3] |
| *Past Medical History* | | | | |
| Hypertension | n = 42 (95.5%) | n = 40 (97.6%) | n = 48 (94.1%) | n = 50 (94.3)% |
| Coronary Artery Disease | n = 18 (40.9%) | n = 16 (39.0%) | n = 18 (35.3%) | n = 19 (35.8%) |
| Diabetes | n = 23 (52.3%) | n = 21 (51.2%) | n = 27 (52.9%) | n = 26 (49.1%) |
| COPD | n = 10 (22.7%) | n = 9 (22.0%) | n = 12 (23.5%) | n = 10 (18.9%) |
| HF hospitalization in last year | 20/29 (69.0%) | 19/31 (61.3%) | 23/34 (67.6%) | 23/37 (62.2%) |
| Ejection fraction (%)[a,b] | 45.4 [14.9] | 44.3 [14.0] | 45.0 [15.1] | 45.1 [14.0] |
| *Baseline VAS, Lab Results, and X-ray Results* | | | | |
| Baseline dyspnea VAS (mm)[a] | 65.0 [18.8] | 67.7 [20.6] | 64.8 [18.0] | 64.8 [21.2] |
| BUN (mg/dl)[a] | 19.6 [13.5] | 19.8 [13.4] | 21.3 [15.4] | 26.4 [40.3] |
| Creatinine (mg/dl)[a] | 1.4 [1.0] | 1.4 [1.1] | 1.6 [1.4] | 2.1 [4.3] |
| Sodium (mmol/l)[a] | 139.5 [6.4] | 141.5 [4.7] | 139.8 [6.1] | 141.8 [4.6] |
| cTnT > 0.1 ng/ml | 6/36 (16.7%) | 8/30 (26.7%) | 8/43 (18.6%) | 12/41 (29.3%) |
| BNP (pg/ml)[a] | 894.5 [755.4] | 924.5 [952.3] | 948.2 [954.3] | 1022.9 [1122.9] |
| Confirmed AHF | | | | |
| Chest x-ray | n = 15 (34%) | n = 10 (24%) | n = 15 (29%) | n = 12 (23%) |
| Laboratory | n = 14 (32%) | n = 9 (22%) | n = 14 (28%) | n = 11 (21%) |
| Both | n = 15 (34%) | n = 22 (54%) | n = 15 (29%) | n = 22 (42%) |
| Total | n = 44 (100%) | n = 41 (100%) | n = 44 (86%) | n = 45 (85%) |
| Baseline SBP[a] | 189.5 [26.4] | 187.5 [20.5] | 188.2 [25.0] | 184.8 [21.9] |
| *Systolic Blood Pressure Targets* | | | | |
| High SBP Target (mmHg)[a] | 156.7 [14.5] | 155.6 [13.9] | 155.6 [14.1] | 153.8 [15.4] |
| % difference between initial SBP and high target[a] | −16.5 [8.7] | −16.5 [7.4] | −16.6 [8.4] | −16.2 [8.4] |
| Low SBP Target (mmHg)[a] | 130.0 [13.1] | 129.0 [14.5] | 129.1 [12.9] | 127.8 [14.6] |
| % difference between initial SBP and low target[a] | −30.6 [8.8] | −30.9 [7.0] | −30.7 [8.4] | −30.4 [7.7] |

[a] = reported as mean [standard deviation]
[b] = for Safety population: n = 26 for patients receiving clevidipine, n = 26 for patients receiving SOC for AHF population: n = 23 for patients receiving clevidipine, n = 22 for patients receiving SOC
COPD = chronic obstructive pulmonary disease;
BUN = blood urea nitrogen;
cTnT = cardiac troponin T The initial clinical diagnosis of AHF was confirmed after study drug administration by chest X-ray and/or natriuretic peptide assessment. Historical ejection fraction data was recorded when available. Also, the safety of a prolonged clevidipine infusion (up to 96 hours per protocol) compared to intravenous SOC was assessed by laboratory parameters, adverse events through 7 days or discharge (whichever occurred first), and serious adverse events through 30 days following randomization.

Table 2 shows the administration of the study drug during the first 30 minutes and thereafter. Most (86.8%) safety patients receiving SOC were administered either nitroglycerin (56.6%) or nicardipine (30.2%) (Table 2). The mean [standard deviation (SD)] door-to-study drug time was 3.2 h [1.9 h] and 2.7 h [1.8 h] (p=0.243) for the patients receiving clevidipine and SOC, respectively.

Figure 1:
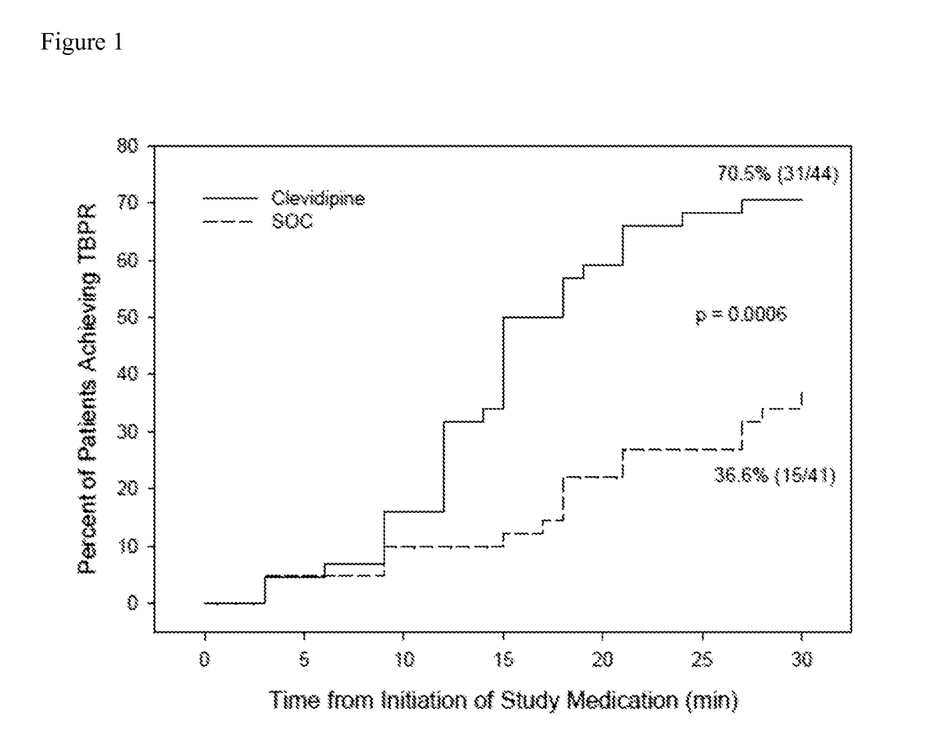
FIG. 1 compares the percentage of patients who achieved the target blood pressure range for patients who were administered clevidipine and for patients who were administered the standard of care (SOC) therapy.

The target blood pressure range was achieved more reliably in patients treated with clevidipine (31/44, 70.5%) than those treated with the SOC (15/41, 36.6%) (p=0.002). For patients in which the target blood pressure range was achieved, those treated with clevidipine reached this target in a median time of 15 min (interquartile range (IQR) of 12-18 min) as opposed to 18 min (IQR of 9-27 min) for those treated with the SOC (p=0.0006) (see FIG. 1).

TABLE 2

Intravenous Antihypertensive Study Drug Dosing (safety population)

| Time Frame | Drug Name (n), dosing unit | Mean of Individual Patient Median Infusion Rates [SD] | Infusion Rates (min, max) | Mean of Total Dose Administered [SD] |
| --- | --- | --- | --- | --- |
| Initiation of Study Drug to 30 minutes | Clevidipine (51), mg/h | 6.4 [3.4] | 1.0, 16.0 | 4.6 [3.1] |
| | SOC Medications | | | |
| | Nitroglycerin (30), mg/h | 40.8 [40.9] | 3.3, 200 | 1.3 [1.4] |
| | Nicardipine (16), mg/h | 6.2 [2.6] | 1.0, 10.0 | 3.2 [1.4] |
| | ISDN (4), mg/h | 180.5 [254.1] | 1.0, 540 | 4.75 [4.9] |
| | Hydralazine (1), mg | — | — | 20 (single bolus) |
| | Diltiazem (1), mg | — | — | 5 (single bolus) |
| | Nitroprusside (1), mcg/min | 13.3 | 13.3, 13.3 | 0.4 |
| From 30 minutes until infusion stopped | Clevidipine (51), mg/h | 7.6 [5.4] | 1.0, 24.0 | 24.6 [36.9] |
| | SOC Medications | | | |
| | Nitroglycerin (30), mg/h | 65 [60] | 3.3, 233 | 55.3 [97.5] |
| | Nicardipine (16), mg/h | 8.2 [4.0] | 1.0, 15.0 | 15.4 [13.0] |
| | ISDN (4), mg/h | 61 [103.3] | 1.0, 180 | 12.01 [4.8] |
| | Hydralazine (1), mg | — | — | — |
| | Diltiazem (1), mg | 10 | 10, 10 | 38.7 |
| | Nitroprusside (1), mcg/min | 13.3 | 13.3, 13.3 | 3.0 |

ISDN = isosorbide dinitrate

In addition, patients treated with clevidipine required fewer additional antihypertensives (15.9% vs 51.2%, p=0.0005). The majority in both groups received diuretics (75% of patients receiving clevidipine, 83% of patients receiving SOC), although of those patients who were administered furosemide (75% of patients receiving clevidipine, 76% of patients receiving SOC) the patients receiving clevidipine were administered lower doses (58.2 mg vs. 78.1 mg, p=0.006).

Patients receiving clevidipine and patients receiving SOC had similar rates of being within, but not below, the target blood pressure range (45.5% vs. 51.2%, respectively; p=0.059). In the first 30 minutes of the study, no patient had a SBP below 102 mmHg. Overall, 16 patients exceeded their lower target blood pressure range limit; 15 patients receiving clevidipine and 1 patient receiving SOC (p<0.001) exceeded the lower limit by a mean of 8.7 mmHg and 13 mmHg, respectively. Yet, no patient developed signs or symptoms of hypoperfusion on a study drug.

For the remainder of the study, an SBP <90 mmHg occurred in 3 patients receiving clevidipine (5.9%), which lasted a median (IQR) of 3.3 minutes (1.3, 6.6), and in 1 patient receiving SOC (1.9%), which lasted 13 minutes. The proportion of time that the SBP was <90 mmHg while on a study drug was 2.5% and 1.1% for patients receiving clevidipine and patients receiving SOC, respectively (p=0.510). Symptomatic hypotension occurred in one patient who received clevidipine, at 3.5 hours after the administration of clevidipine was terminated. There were no differences in blood pressure response related to ejection fraction Finally, mean [SD] heart rate changes from baseline to 30 minutes were similar between patients receiving clevidipine (2.6 bpm [10.6 bpm]) and patients receiving SOC (1.1 bpm [8.4 bpm]) (p=0.424).

The area under the curve (AUC) outside the target blood pressure was lower in patients treated with clevidipine as compared to patients treated with SOC (median of 379 mmHg×min/h and an IQR of 192-608 mmHg×min/h, vs. median of 755 mmHg×min/h and an IQR of 374-1172 mmHg×min/h) (p=0.002). The AUC above the target blood pressure was also lower in patients receiving clevidipine than in patients receiving SOC, with a median of 327 mmHg×min/h and an IQR of 169-608 mmHg×min/h for clevidipine-administered patients as opposed to a median of 755 mmHg×min/h and an IQR of 368-1172 mmHg×min/h for SOC-administered patients (p=0.0007). On the other hand, the AUC below the target blood pressure was greater for patients treated with clevidipine than with SOC, with medians of 0 mmHg×min/h for both groups and IQRs of 0-42 mmHg×min/h and 0-0 mmHg×min/h, respectively (p=0.003).

Endotracheal intubation was required in only one patient receiving SOC. Five patients expired within 30 days of treatment (3 patients receiving clevidipine, 2 patients receiving SOC; p=0.615), and none during the administration of the study drug. None of these events were considered to be study drug-related by the investigator or the Data and Safety Monitoring Board, which independently monitored patient safety throughout the study. Patients receiving clevidipine and patients receiving SOC had a similar incidence of serious adverse events (23.5% vs. 18.9%, respectively; p=0.561) and drug related treatment-emergent adverse events (TEAEs) (9.8% vs. 13.2%, respectively; p=0.587) (see Table 3). Mild to moderate headache, which occurred predominately in patients receiving SOC, was the most common TEAE. There were no clinically significant differences in the frequency of TEAE between the treatment groups.

TABLE 3

Study Drug Related Treatment-Emergent Adverse Events (safety population)

| Category | Clevidipine (n = 51) | SOC (n = 53) | Total (n = 104) |
|---|---|---|---|
| Patients with at least one related TEAE | n = 5 (9.8%) | n = 7 (13.2%) | n = 12 (11.5%) |
| Preferred Term | | | |
| Headache | n = 1 (2.0%) | n = 7 (13.2%) | n = 8 (7.7%) |
| Abdominal discomfort | n = 1 (2.0%) | n = 0 (0%) | n = 1 (1.0%) |
| Abdominal pain | n = 1 (2.0%) | n = 0 (0%) | n = 1 (1.0%) |
| Flushing | n = 1 (2.0%) | n = 0 (0%) | n = 1 (1.0%) |
| Myalgia | n = 1 (2.0%) | n = 0 (0%) | n = 1 (1.0%) |
| Nausea | n = 1 (2.0%) | n = 0 (0%) | n = 1 (1.0%) |
| Ventricular tachycardia | n = 1 (2.0%) | n = 0 (0%) | n = 1 (1.0%) |
| Blurred vision | n = 1 (2.0%) | n = 0 (0%) | n = 1 (1.0%) |

While patients receiving clevidipine and patients receiving SOC had similar rates of diagnostic procedures (14 patients (27.5%) and 12 patients (22.6%), respectively) (p=0.571), patients receiving clevidipine had fewer therapeutic procedures (0 patients (0%) vs. 9 patients (17%)) (p=0.003), which was defined as arterial line, intubation, defibrillation, pacemaker placement, dialysis, coronary revascularization and/or surgery. Patients receiving clevidipine also had non-significant trends to fewer hospital admissions (90.2% vs 98.1%) (p=0.083), fewer ICU admissions (22.9% vs. 26.9%) (p=0.644), shorter median hospital stays (4.0 days vs. 5.0 days) (p=0.235), fewer 30-day all cause emergency department/hospital readmissions (14.9% vs. 16.7%) (p=0.813), and longer out-of-hospital periods before re-hospitalization (11.0 days vs. 5.0 days) (p=0.092).

These results suggest that the use of clevidipine may be safe and effective in hypertensive AHF patients. In addition, the AUC results demonstrate that blood pressure control was better in patients receiving clevidipine as compared to patients receiving SOC.

Example 2

Clevidipine Improves Dyspnea Associated with Acute Heart Failure

The effect of clevidipine on dyspnea was assessed in the patients described in Example 1. Dyspnea was assessed by a 100 mm VAS, in which a score of 0 was "no dyspnea" and a score of 100 represented "worst possible dyspnea." Dyspnea was evaluated immediately prior to study drug administration, and at 15, 30, 45, 60, 120, 360 and 720 minutes afterward. In addition, the Vasodilation in the Management of Acute Congestive Heart Failure (VMAC) scale, a relative 7 point Likert score, and the Provocative Dyspnea Assessment (PDA) (Pang et al, *Eur Heart J* 2008, 29) were both performed in the seated and supine positions and recorded.

Figure 2A:
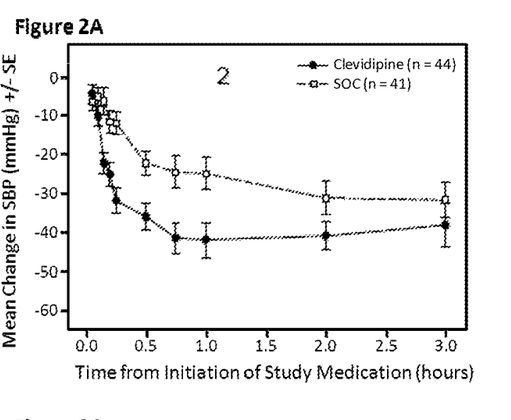
FIGS. 2A and 2B compare the mean change in SBP between clevidipine and the SOC and between clevidipine and SOC subsets (nitroglycerine and nicardipine), respectively, during the first three hours of administration.
Figure 2B:
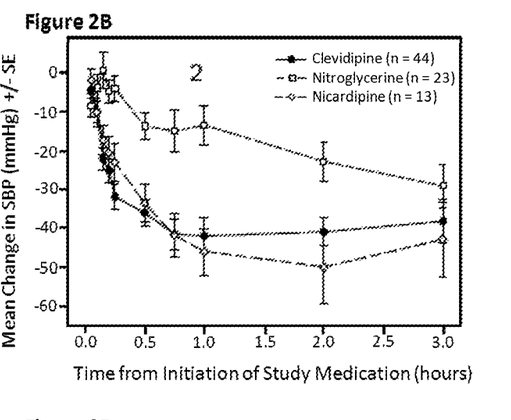
Figure 2C:
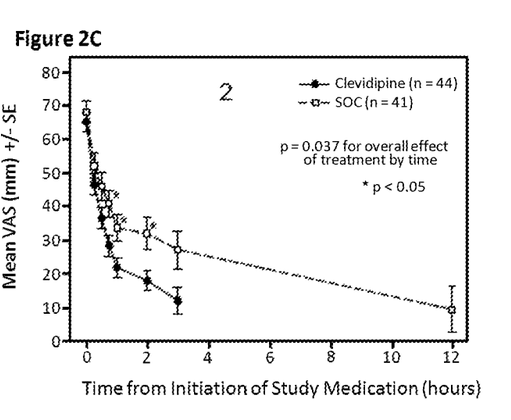
FIGS. 2C and 2D compare the mean VAS score between clevidipine and the SOC and between clevidipine and SOC subsets (nitroglycerine and nicardipine), respectively, during the first 12 hours of administration.

In the first 30 minutes after study drug administration, there was a marked dyspnea improvement that paralleled the blood pressure decrease in both groups (compare FIGS. 2A and 2C). At 45 minutes, the mean [SD] VAS decrease from baseline was greater in the patients treated with clevidipine, as compared to patients receiving SOC (37.1 mm [20.9 mm] vs. 27.9 mm [7.1 mm]) (p=0.02). The greater effect on dyspnea in the clevidipine-administered patients was maintained to the 3 hour mark. For example, VAS dyspnea scores for the clevidipine and SOC patients were 21.7 [18.79] mm and 33.4 [24.93] mm, respectively (p=0.0203), at 1 hour after administration of the study drugs, and 17.8 [16.0] mm and 31.8 [25.5] mm, respectively (p=0.0152), at 2 hours after administration of the study drugs.

Over time, VAS dyspnea scores decreased more from baseline with clevidipine than SOC (treatment×time effect, p=0.037), and the VMAC and PDA scores had non-significant trends toward greater improvement with clevidipine than SOC.

Figure 2D:
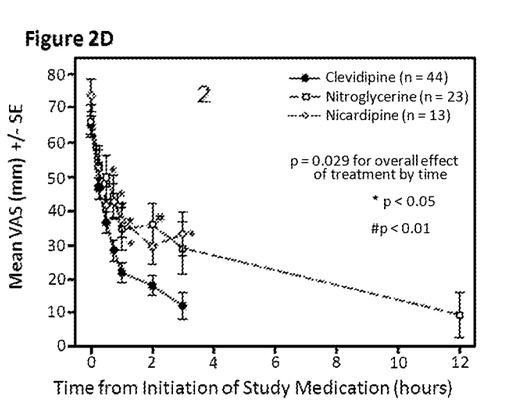

The decrease in VAS and SBP over time for the nitroglycerin and nicardipine subsets of SOC were also assessed (FIGS. 2B and 2D). Nicardipine reduced SBP similarly to clevidipine, but neither nitroglycerin nor nicardipine improved VAS as quickly as clevidipine.

Like clevidipine, nicardipine is an L-type calcium channel blocker and is in the same pharmacologic class of agents as clevidipine, but the effect of clevidipine on dyspnea was significantly greater than the effect of nicardipine on dyspnea. Without wishing to be bound by theory, this suggests that clevidipine may have a unique effect on relieving dyspnea.

These results demonstrate that clevidipine leads to a faster and more pronounced improvement in dyspnea in patients suffering from heart failure than SOC therapy. Further, the results suggest that clevidipine may act in particular as a dyspnea reduction agent.

Example 3

Clevidipine May Improve Dyspnea in Acute Heart Failure Patients with SBP Below 160 mmHg A controlled investigation is being conducted on the effects of clevidipine, as compared to a placebo or SOC, on patients with AHF, SBP ≥120 mmHg, and moderate-to-severe dyspnea (defined as ≥50 mm on a 100 mm self-reported VAS).

The investigation is divided into two stages: stage 1, which is a double blind study that will compare the effects of clevidipine and a placebo, and stage 2, which is an open label study that will compare the effects of clevidipine with SOC.

Enrollment

In stage 1, patients will be enrolled and randomized in a double-blind fashion, based on a clinical diagnosis of AHF by the attending physician, to receive either clevidipine or matching intravenous placebo in a 1:1 ratio. All patients will be randomized and treated within three hours of presentation to the emergency department. The patients will be allowed to receive all supportive therapy per the direction of the treating physician except intravenous antihypertensive medications including nitrates. Randomization for stage 1 will be stopped after 100 patients are confirmed to have AHF, which is performed post-hoc and is defined as a BNP >400 pg/ml, or NTproBNP >900 pg/ml, or by the presence of congestion on a chest X-ray. Blood pressure treatment goals will be defined according to whether the baseline SBP of the patient is in the range of 120 mmHg to less than 140 mmHg (120-<140 mmHg), or 140 mmHg to 160 mmHg (≥140-160 mmHg). In the higher SBP stratum, blood pressure goals will be determined by the treating physician recording a target blood pressure range to reach a minimum 15% blood pressure reduction from baseline. In patients presenting in the lower SBP stratum, the target blood pressure range should be no lower than 110 mmHg.

Stage 2 will be identical to stage 1, but will have an enrollment of 300 patients and will be randomized in an open label fashion to receive either clevidipine or SOC treatment in a 1:1 ratio. Randomization will be stopped after 300 patients are confirmed to have AHF. Notably, if patients with baseline SBP from 120 mmHg to <140 mmHg are less short of breath on presentation and are thereby exhibiting smaller effect size, then patients with baseline SBP from 120 mmHg to <140 mmHg may not be enrolled in Stage 2. Otherwise, stage 2 will involve patients with a baseline SBP of ≥120 mmHg.

Overall inclusion and exclusion criteria for both studies are shown in Table 2:

TABLE 2

Inclusion and Exclusion Criteria.

| Inclusion Criteria | Exclusion Criteria |
| --- | --- |
| Age 18 years or older and providing written informed consent<br>Presentation consistent with AHF as manifest by pulmonary congestion and the presence of rales or abnormal chest radiography<br>Dyspnea score (sitting) ≥50 mm on a 100 mm visual analog scale<br>Baseline SBP ≥120 mmHg (measured immediately prior to initiation of the study drug (i.e., clevidipine, placebo, or SOC)) | Administration of an IV or oral antihypertensive agent within the previous 2 hours of randomization (short acting non-IV nitrates are permitted)<br>Chest pain and/or electrocardiogram (ECG) with ST segment changes consistent with acute coronary syndrome<br>Known or suspected aortic dissection<br>Acute myocardial infarction (AMI) within the prior 14 days<br>Dialysis dependent renal failure<br>Requirement for immediate endotracheal intubation<br>Suspected pregnancy or breast feeding female<br>Intolerance or allergy to calcium channel blockers<br>Allergy to soybean oil or lecithin<br>Known liver failure, cirrhosis or pancreatitis<br>Prior directives against advanced life support (no code status)<br>Participation in other clinical research studies involving the evaluation of other investigational drugs or devices within 30 days of enrollment |

Stage 1 Protocol for Administering the Study Drug

In stage 1, prior to randomization, a patient-specific SBP target range for the desired blood pressure reduction must be predetermined The difference between the upper and lower limits of the target blood pressure range should not be less than 20 mmHg and not more than 40 mmHg, and in no case should the lower limit of the target SBP range be less than 110 mmHg. SBP lower than 90 mmHg will be considered as hypotension. For patients randomized to clevidipine or placebo, the dosing will be per the approved label and the infusion must be administered intravenously at an initial rate of 2 mg/h; this rate will be maintained for the first 1.5 min (90 seconds). If the target reduction in SBP is not achieved within 1.5 minutes using a dose of 2 mg/h, the clevidipine infusion may be titrated in doubling increments every 1.5 min as tolerated by the patient, to achieve an SBP within the pre-specified target range. The clevidipine infusion rate may also be decreased in order to achieve an SBP within the target blood pressure range. The minimum infusion rate is 1 mg/h and the maximum infusion rate will not exceed 32 mg/h. If the target blood pressure range is achieved at any of the titration doses, that rate may be continued for as long as necessary to maintain the target blood pressure range for up to 24 hours. If the desired blood pressure lowering effect is not attained with the study drug within 30 minutes or is not maintained thereafter, any alternative antihypertensive agent may be used, with or without stopping the study drug infusion.

The alternative agent should be used per institutional treatment practice. During the initial 30 min of the treatment period, however, the study drug should be administered as a monotherapy with the exception of diuretics and morphine. The study drug infusion may be terminated at any time for a safety reason.

Clevidipine will be administered as Cleviprex®, which is a ready-to-use, sterile, white opaque, oil-in-water emulsion for intravenous administration. It will be supplied in 50 ml Type I clear glass vials, fitted with a grey rubber stopper and sealed with aluminum over seal.

The placebo will be supplied in 50 ml Type I clear glass class vials identical to the clevidipine vials, and will be filled with identical ready-to-use, sterile, white opaque, 20% oil-in-water emulsion (Intralipid®) for intravenous administration.

Clevidipine or the placebo will be administered for a minimum of 30 minutes and a maximum duration of 24 hours as determined by the investigator. Patients will be followed for 3 hours post study drug termination.

Stage 2 Protocol for Administering the Study Drug

In stage 2, prior to randomization, a patient-specific target blood pressure range for the desired blood pressure reduction must be predetermined The difference between the upper and lower limits of the target blood pressure range should not be less than 20 mmHg and not more than 40 mm Hg, and in no case should the lower limit of the target blood pressure range be less than 110 mmHg. SBP lower than 90 mmHg will be considered as hypotension. The infusion of clevidipine must be administered intravenously at an initial rate of 2 mg/h; this rate will be maintained for the first 1.5 min (90 seconds). If the target reduction in SBP is not achieved within 1.5 minutes using a dose of 2 mg/h, the clevidipine infusion may be titrated in doubling increments every 1.5 min as tolerated by the patient, to achieve an SBP within the target blood pressure range. The clevidipine infusion rate may also be decreased in order to achieve an SBP within the target blood pressure range. The minimum infusion rate is 1 mg/h and the maximum infusion rate will not exceed 32 mg/h.

If the desired blood pressure lowering effect is not attained with the study drug within 30 minutes or not maintained thereafter, any alternative antihypertensive agent may be used, with or without stopping the study drug infusion. The alternative agent should be used per institutional treatment practice. During the initial 30 minutes of the treatment period, however, the study drug should be administered as monotherapy. The use of an alternative antihypertensive agent(s) (rescue therapy) or changing the target blood pressure range is discouraged and limited to where medically necessary to maintain patient safety.

For patients randomized to SOC, the infusion must be continuous and administered per the institution's treatment practice, and dose titration must be performed to a maximum allowed or maximum tolerated dose to achieve target SBP.

Clevidipine will be administered as Cleviprex®, which is a ready-to-use, sterile, white opaque, oil-in-water emulsion for intravenous administration. It will be supplied in 50 ml Type I clear glass vials, fitted with a grey rubber stopper and sealed with aluminum over seal.

Clevidipine will be administered for a minimum of 30 minutes and a maximum duration of 24 hours as determined by the investigator. Patients will be followed for 3 hours post study drug termination.

Evaluation of the Patients

Both stages will evaluate the percent change in the patients' dyspnea baseline VAS score occurring at 3 hours after the initiation of the study drug. In addition, the studies will determine if there is a change in the patients' dyspnea baseline VAS score over time, the median time to reach target blood pressure range within the first 30 minutes, and the percentage of patients who require rescue therapy (i.e., receive any alternative IV antihypertensive drug) within 30 minutes of initiating the study drug. Patients will be evaluated for dyspnea, as measured using VAS, at 0, 15 min, 30 min, 45 min, 1 h, 2 h, and 3 h after initiation of the study drug, and the sooner of either 12 h after initiation of the study drug or 1 h after discontinuation of the study drug. In addition, the EDTA plasma of the patients will be assessed for troponin I, B-type natriuretic peptide, galectin-3, and ST-2, at baseline, 3±1 h, and 24±6 hours following initiation of the study drug.

Further, the studies will explore the safety of a prolonged infusion of clevidipine as compared to the placebo or SOC (up to 24 hours), and will monitor adverse events up to 7 days or discharge (whichever occurs first) and serious adverse events through 30 days following randomization of the patients at enrollment. The studies will also determine the presence of improved health economic parameters associated with use of clevidipine, including therapeutic and diagnostic procedures, hospital and ICU admissions, hospital and ICU length of stay, ICU length of stay, and frequency of 30 day revisits. In addition, the patients' need for polypharmacy will be assessed.

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of reducing dyspnea in a patient in need thereof, wherein the patient has acute heart failure and is initially normotensive as determined by the patient's baseline systolic blood pressure, the method comprising only administering a pharmaceutical composition comprising only one active pharmaceutical ingredient, wherein the only one active pharmaceutical ingredient is clevidipine, to the patient.

2. The method of claim 1, wherein the patient has a baseline dyspnea score of at least about 50 mm using a 100 mm visual analog scale.

3. The method of claim 1, wherein the reduction in dyspnea is determined by a decrease in a dyspnea score using a visual analog scale.

4. The method of claim 1, wherein the pharmaceutical composition is administered as an intravenous infusion.

5. The method of claim 4, wherein the intravenous infusion is administered at a rate between about 1 mg/h and about 32 mg/h of clevidipine.

6. The method of claim 4, wherein the intravenous infusion is administered for a duration of about 30 minutes to about 72 hours.

7. The method of claim 4, wherein the intravenous infusion is administered at an initial rate of about 2 mg/h of clevidipine.

8. The method of claim 7, wherein the intravenous infusion administered at the initial rate of about 2 mg/h is maintained at the initial rate for at least about 90 seconds.

9. The method of claim 8, further comprising titrating the intravenous infusion to a rate that maintains the patient's systolic blood pressure at no less than about 110 mmHg.

10. The method of claim 1, wherein the method additionally controls, maintains, or reduces the patient's systolic blood pressure.

* * * * *